United States Patent [19]

Rinno et al.

[11] Patent Number: 5,529,749
[45] Date of Patent: Jun. 25, 1996

[54] PROCESS FOR REDUCING THE MICROBE COUNT IN AQUEOUS MULTI-PHASE COMPOSITIONS THAT CONTAIN SYNTHETIC RESIN

[75] Inventors: Helmut Rinno, Hofheim; Friedrich Hessel, Mainz; Klaus Alberti, Idstein, all of Germany

[73] Assignee: Hoechst Aktiengesellschaft, Frankfurt, Germany

[21] Appl. No.: 353,243

[22] Filed: Dec. 2, 1994

[30]  Foreign Application Priority Data

Dec. 13, 1993 [DE] Germany .......................... 43 42 391.4

[51] Int. Cl.$^6$ .............................. A61L 2/12; C07B 63/00
[52] U.S. Cl. ...................... 422/21; 204/158.21
[58] Field of Search .............................. 422/21; 528/503; 523/122; 427/488, 508, 516, 544, 553, 561; 204/157.15, 158.21

[56]  References Cited

U.S. PATENT DOCUMENTS

| | | | |
|---|---|---|---|
| 3,432,413 | 3/1969 | Vanderhoff | 204/165 |
| 3,551,199 | 12/1970 | Forster | 427/553 |
| 3,624,422 | 7/1972 | Gray | 422/21 |
| 4,008,361 | 2/1977 | Park et al. | 528/503 |
| 4,020,267 | 4/1977 | Park | 528/503 |
| 4,117,220 | 9/1978 | Worman, Jr. | 528/503 |
| 4,948,872 | 8/1980 | Brulet et al. | 528/503 |
| 5,216,122 | 6/1993 | Reichle et al. | 528/503 |
| 5,244,628 | 9/1993 | Ritter et al. | 422/21 |

FOREIGN PATENT DOCUMENTS 9013319  11/1990  European Pat. Off. .
2612572  10/1976  Germany .

OTHER PUBLICATIONS

Block, *Disinfection, Sterilization & Preservation*, 1991, pp. 918–921.
*Patent Abstracts of Japan*, vol. 7, No. 6 (C–157) 18 Mar. 1993, JP–A–57 212 272 (Fujitsu K.K.) 27 Dec. 1982.
*Derwent Publications Ltd.*, Section CH, Week 9431, London, G.B., Class ADE, AN 94–253876 C31 and SU–C–2 005 494 (Med. Polymers Res. Inst.), 15 Jan. 1994.
*Patent Abstracts of Japan*, vol. 10, No. 156 (C–351) 5 Jun. 1986, JP–A–61 012 769 (Canon K.K.) 21 Jan. 1986.
*Patent Abstracts of Japan*, vol. 18, No. 476 (C–1246) 6 Sep. 1994, JP–A–06 154 304 (Nitto Denko Corp.), 3 Jun. 1994.
*Derwent Publications Ltd.*, Section Ch, Week 8325, London, G.B., Class DMA, AN–83–60441K C25, JP–A–58 081 996 (Toyota Motor K.K.) 17 May 1993.
Wallhausser, et al., "Preservation of Awueous Plastics Dispersions", *Farbe und Lack*, vol. 91:277–286, (1985).
Koch, "The Use of Microwave Technology for Preserving Foodstuffs," *Lebensmitteltechnik*, vol. 1–2:39–43, (1989).
Wallhauser, "Practice of Sterilzation", Disinfection–Preservation, 4th Edition, p. 250, (1988).

*Primary Examiner*—Robert J. Warden
*Assistant Examiner*—Theresa T. Snider
*Attorney, Agent, or Firm*—Foley & Lardner

[57]  ABSTRACT

A process is disclosed for reducing the microbe count in microbially-contaminated aqueous multi-phase composition containing synthetic resin, such as polymer dispersions and formulations that contain polymeric binders. The process uses dielectric heating, preferably immediately before transfer of the multi-phase composition to containers.

22 Claims, No Drawings

PROCESS FOR REDUCING THE MICROBE COUNT IN AQUEOUS MULTI-PHASE COMPOSITIONS THAT CONTAIN SYNTHETIC RESIN

BACKGROUND OF THE INVENTION

The present invention relates to a process for reducing the microbial count in microbially-contaminated aqueous multi-phase compositions that contain synthetic resin, such as polymer dispersions and formulations that comprise polymeric binders, by dielectric heating.

Aqueous multi-phase systems that contain a synthetic resin, for example, polimer dispersions and dispersion-bonded systems for the adhesives or paints sector, are threatened by microbial attack and microbial decomposition. Temperatures of about room temperature and pH values in the neutral to slightly alkaline range represent good growth conditions for bacteria, yeasts and fungi. These microorganisms are everywhere in the environment. Various microorganisms have been detected in dispersions of plastics (K. H. Wallhäuser, W. Fink, Die Konservierung von wäβrigen Kunststoff-Dispersionen, [PRESERVATION OF AQUEOUS PLASITCS DISPERSIONS], Farbe und Lack 91, 277 (1985)); bacteria: Pseudomonas, Enterobacteriaceae, Bacillus species fungi: Aspergillus, Penicillium, Cephalosporium, Fusarium; yeasts: Saccharomyces. Uninhibited growth of such microorganisms leads to clearly perceptible external changes, for example, the occurrence of an unpleasant smell or visible mold growth, as well as to a change in important applications properties, for example, the viscosity or the pH.

The desired value for the microbial count is not more than 1000 microbes per ml, a value which complies with the guidelines of the Drinking Water Act of 1986 (BGB1. I No. 22, 760, 1986) for water at 18–22° C. from collection and storage tanks.

Various chemical and physical methods are described for preventing attack or for reducing the risk of an attack by microorganisms, for example, in Wallhäuser, Praxis der Sterilisation, Desinfektion-Konservierung [Practice of sterilization and disinfection/preservation], 4th Edition, Georg Thieme Verlag, Stuttgart, 1988. The method most frequently used in practice for preservation or sterilization entails the addition of substances that have a microbicidal action, such as bactericides and fungicides. The chemical preservatives used are subject to strict approval proceedings, and therefore only a limited number are available. Because of toxic or allergenic properties they may be employed only in small amounts, but can nevertheless cause health disorders in sensitive persons in isolated cases. Particularly active preservatives, for example, formaldehyde or products which split off formaldehyde, may not be used at all within wide fields of use for a formulation according to BGA [Federal Board of Health] guidelines. Another problem in the use of chemical preservatives is the increasing resistance of various microbes.

Aqueous multi-phase compositions that contain synthetic resin, such as polymer dispersions, dispersion adhesives, emulsion paints for internal and external use, primers and plasters based on dispersions, concrete auxiliaries, paper-coating compositions, leather finishes, cheese-covering compositions and dispersions of polycondensation products, which are prepared in situ or as a secondary dispersion, have a complex colloidchemical structure which protects them from phase separation on the basis of electrostatic, steric or electrosteric stabilization mechanisms. To obtain the desired technical properties, this system must persist in particular in respect of its material composition and its state of division during preparation, storage and transportation up to application. This is generally no longer the case after a massive multiplication of microorganisms. A number of physical and chemical treatment methods therefore already have been tried, to avoid the use of microbicides or to limit them in terms of amount. Sterilization by means of known physical methods, for example, by heat treatment or by treatment with γ-rays, produces a change in this complex colloid-chemical structure. Heat treatment of a polymer dispersion by means of indirect heating leads to adequate microbe reduction only at high temperatures over long residence times (121° C., 3 min). However, after only a short time, a heavy deposit forms on the heat exchanger walls, a coagulate forms or the particle size distribution changes due to a disturbance in the colloid-chemical composition. The formation of a deposit then produces further overheating as a result of an increased heat transfer resistance, and therefore to increased deposits. These deposits comprise, for example, coagulated polymer particles which can no longer be redispersed in the case of heat treatment of a dispersion, and coagulated polymer particles which have enclosed pigments and/or fillers in the case of heat treatment of a paint. The use of γ-rays, for example, from a $^{60}Co$ source, in the presence of oxygen and water leads to formation of hydrogen peroxide and of hydroxyl radicals, which trigger undesirable side reactions and cause crosslinking of the polymer. These physical stabilization methods are therefore unsuitable for an industrially feasible sterilization of aqueous multi-phase compositions that contain synthetic resin.

The use of microwave radiation for heating is known for sterilization in the foodstuffs sector and for pharmaceutical products (K. H. Wallhäuser, PRAXIS DER STERILISATION [PRACTICE OF STERILIZATION] (4th Edition), Desinfektion-Konservierung [Disinfection-Preservation], georg Thieme Verlag, Stuttgart, 1988, p. 250). Koch also describes the use of microwave technology for sterilizing foodstuffs (K. Koch, ÜBER DEN EINSATZ DER MIKROWELLENTECHNIK ZUM HALTBARMACBEN VON LEBENSMITTELN [THE USE OF MICROWAVE TECHNOLOGY FOR PRESERVING FOODSTUFFS], Lebensmitteltechnik, 1–2, pages 39–43, 1989).

In the foodstuffs sector, microwave radiation is used exclusively to heat the products to be sterilized to a certain temperature. The exposure time needed for inactivation/destruction of the microorganisms must be ensured, for example, in a subsequent heat retention tunnel. The temperature of at least 121° C. mentioned in the literature which is necessary for sterilizing corresponds precisely to the temperature which is necessary for sterilizing by means of other heat processes. Based on this fact, this method should be unsuitable for the complex multi-phase compositions that contain synthetic resin, since the high temperatures required trigger the changes already described, in particular coagulation of the complex composition.

The use of microwave beams for the preparation of polymer dispersions is already known from U.S. Pat. No. 3 432 413. The reduction of the residual monomer content in vinyl halide dispersions by means of microwave radiation is described in U.S. Pat. No. 4 117 220 and DE-A 26 12 572.

SUMMARY OF THE INVENTION

An object of the present invention is to provide a process for reducing the microbial count in an aqueous multi-phase composition that contains a synthetic resin which is carried out at moderate temperatures and does not have the disadvantages described for the known processes.

These and other objects according to the invention are achieved by a process for reducing the microbe count in a microbially-contaminated aqueous multi-phase composition that contains synthetic resin, the process including a step of dielectric heating an aqueous multi-phase composition that contains a synthetic resin. In a preferred embodiment, the dielectric heating is carried out by means of a microwave apparatus, preferably at a microwave frequency of 0.04 to 24 GHz. It is preferred that the aqueous multi-phase composition flow continuously through the microwave apparatus.

According to the invention an aqueous multi-phase composition preferably is subjected to a sterilization temperature of below 121° C., more preferably to a temperature is between 50° and 100° C. In a preferred embodiment, the process is carried out under an autogenous pressure of up to 10 bar.

The process can be used to sterilize polymer dispersions, as well as formulations that comprises a polymer dispersion. In particular, the polymer dispersion is an emulsion polymer that contains acrylate or vinyl acetate groups.

Preferably, the dielectric heating is carried out immediately before the aqueous multi-phase composition is transferred to containers. An additional step of adding a microbicide to the aqueous multi-phase composition can be included in the process. In this case, the amount of microbicide added is less than 50% of the amount of microbicide necessary to achieve sterilization for an identical aqueous multi-phase composition which has not been subjected to dielectric heating.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF PREFERRED EMBODIMENTS

Surprisingly, it has been found that the temperatures necessary for microbe reduction or sterilization are significantly lower with dielectric heating of an aqueous multi-phase composition that contains synthetic resin by microwave radiation than by the conventional introduction of energy, so that an increase in temperature which damages the product can be avoided. It has been found, surprisingly, that no disturbance in the colloidchemical state, such as coagulate formation or formation of a wall deposit, occurs by heating dispersions to temperatures even above 100° C. with the aid of microwave radiation.

The present invention relates to a process for reducing the microbe count in microbially-contaminated aqueous multi-phase compositions that contain a synthetic resin by dielectric heating.

The dielectric heating of the aqueous multi-phase composition preferably is carried out by microwave irradiation. The process according to the invention can be operated by means of various microwave apparatuses. A microwave frequency of 0.04 to 24 GHz, in particular of 0.4 to 2.5 GHz, preferably is used. Microwave frequencies of about 433 MHz, 915 MHz and 2.45 GHz are especially preferred.

The sterilization can be carried out discontinuously (batchwise). Preferably, however, a microwave apparatus for continuous operation is used. This can be followed, if appropriate, by a heat-holding zone. The working parameters, for example, laminar or turbulent flow, use of mixers or special pumps, depend on the particular apparatus employed, but are to be optimized with little outlay such that the aqueous multi-phase compositions that contain synthetic resin are exposed to as little temperature and shear stress as possible.

The sterilization temperatures are below 121° C., preferably between 50° and 100° C., in particular between 60° and 90° C. The sterilization times depend on the apparatus-related amount flowing through and the temperature required, and on the microwave output available. The sterilization is carried out under normal pressure or, preferably, under increased pressure, in order to prevent foaming or formation of bubbles in the product. The pressure used for conveying in the continuous process and/or for suppressing foaming or the formation of bubbles is preferably up to 10 bar, in particular 1–6 bar, above normal pressure. To avoid the formation of bubbles, in the case of which an undesirable skin formation may occur on the surface of the dispersion exposed to the gas space, it also may be advantageous for an increased composition internal pressure to be established externally, for example, by the product delivery pump together with a reducing valve at the end of the sterilization zone, or else by an inert gas. The optimum parameters of the process according to the invention must be determined within the limits mentioned as a function of the particular composition of the aqueous composition that contains synthetic resin. In particular, the temperature and duration of sterilization depend on the composition and stability of the colloid-chemical composition and on the microbes to be destroyed. For example, the optimum temperature for microwave sterilization of a ®Mowilith DM 772 polymer dispersion (dispersion based on acrylic acid/methacrylic acid esters having a solids content of 46% by weight, a viscosity of approx. 3000 mPa.s, a pH of about 8.5 and a density of about 1.06 g/cm$^3$) is 70° C. at a residence time of 1 min in a continuously-operated microwave unit.

Polymer dispersions that have been prepared by means of emulsion polymerization in the presence of free radical initiators, for example, polyvinyl chloride, homo- and copolymeric polyvinyl acetates, polymers of esters of acrylic acid or methacrylic acid with and without a protective colloid, polystyrene, copolymers of styrene and esters of acrylic/methacrylic acid, polybutadiene and copolymers of styrene and butadiene, or aqueous dispersions of polycondensation products, such as polyester resins, polyurethane resins, alkyd resins and epoxy resins, and/or multi-phase compositions which contain synthetic resin and comprise these polymer dispersions, for example, a plaster, adhesive or paint formulation, preferably can be sterilized by means of the process according to the invention.

A particular advantage of the process according to the invention is that aqueous multi-phase compositions that contain synthetic resin, are reliably brought to a uniformly very low microbe count by a microwave treatment. Compositions which have been exposed to the action of microbes during preparation, during storage, during transfer to containers, during transportation or during other manipulations during production, which are frequently customary and unavoidable with industrial processes, can be treated according to the invention up to final packaging. This allows the products then to be transferred to containers under largely sterile conditions, if appropriate completely without the addition of microbicide, and to be stored in closed sterile vessels until used.

Such a possibility previously did not exist over a prolonged storage period, because handling of industrial products, such as paints, plasters and the like, cannot be carried out under sterile conditions throughout the entire course of the production, and also in respect of all the raw materials used. The possibility of microbe reduction in a late stage of fabrication of formulations based on polymer dispersions, moreover, has the advantage that microbes which are introduced into the system from starting substances other than the polymer dispersions, for example, pigments, fillers, foam suppressants, dispersing agents and thickeners, can likewise be destroyed in the finished product.

A particular embodiment of the process according to the invention thus lies in subjecting polymer dispersions or formulations that are based on polymer dispersions to microwave treatment only immediately before the operation of transfer to containers. Either the addition of microbicides can be dispensed with entirely, especially if the formulation is transferred to sterile containers under sufficiently sterile conditions, or the amount of microbicide can be reduced, because of the low microbe count of the transferred material, to less than 50%, preferably less than 20%, of the amount of microbicide otherwise necessary without the intermediate microwave treatment. The amount of microbicide required and the reduction possible are determined by tests on samples with and without microwave treatment. Both variants of the process according to the invention lead to a substantial reduction in the exposure of consumers and the environment to microbicides.

EXAMPLES

The parts and percentages stated in the following examples relate to the weight, unless noted otherwise.
Products used:
Dispersion A:
®Mowillth DM 772 polymer dispersion based on acrylic acid/methacrylic acid ester, 46% solids content, viscosity 3000 mPa.s, pH 8.5, density 1.06 g/cm$^3$
Dispersion B:
®Mowillth DM 2KL dispersion based on vinyl acetate/ maleic acid ester with protective colloid, 45% solids content, viscosity 9000 mPa.s, pH 5, density 1.15 g/cm$^3$
Paint:
Emulsion paint for exterior and interior use according to DIN 53778, comprising 100 parts of Mowilith DM 772, 10 parts of water, 0.4 part of concentrated ammonia, 5.5 parts of a 10% strength aqueous solution of ®Calgon 135 (manufacturer Benkiser, Ladenburg), 0.4 part of ®Genapol PN 30 (manufacturer Hoechst AG, Frankfurt), 0.5 part of foam suppressant ®Agitan 295 (manufacturer Münzing, Heilbronn), 1.8 parts of a 5% strength aqueous solution of ®Borchigel L75 (manufacturer Botchers AG, Düsseldorf), 36.4 parts of titanium dioxide ®Kronos CL 300 (manufacturer Kronos Titan, Leverkusen), 18.2 parts of ®Omya Hydrocarb 90 (manufacturer Omya, Cologne), 6.5 parts of 1, 2-propylene glycol and 1.8 parts of butyldiglycol acetate. The solids content is about 55%, the pigment volume concentration (PVC) is 28% and the density is 1.3 g/cm$^3$.

Microbe count determination, CFU (colony-forming units):
The sample is diluted under sterile conditions (dilution factor 1:100) and applied to two different ready-to-use nutrient media (CSA-agar for bacteria, SDA-agar for yeast/ fungi, manufacturer Merck, Darmstadt) and stored for 5 days at 30° C. in a temperature-controlled incubation cabinet. Evaluation is carried out by counting the colonies, detection limit less than 100 CFU/ml.

1. Heat treatment of dispersions A and B:

Dispersions A and B are heated at various temperatures for a short time by heat treatment in an autoclave, and the microbe count is then determined. At temperatures above 100° C., the dispersions are damaged irreversibly. The results are summarized in Table 1.

TABLE 1

Microbe counts of aqueous multi-phase compositions that contain synthetic resin before/after heat treatment

| | Treatment | | | |
| --- | --- | --- | --- | --- |
| | Temp. [°C.] | Time [min] | CSA [CFU/ml] | SDA Comments |
| Dispersion A | untreated | | 1 · 10$^6$ | 1 · 10$^5$ |
| Dispersion A | 121 | 3 | <100 | <100 coagulate, wall deposit |
| Dispersion A | 121 | 1 | 800 | 500 coagulate, wall deposit |
| Dispersion A | 100 | 1 | 1500 | 1000 wall deposit |
| Dispersion A | 80 | 5 | 1 · 10$^4$ | 1 · 10$^4$ |
| Dispersion B | untreated | | 1 · 10$^5$ | 1 · 10$^5$ |
| Dispersion B | 121 | 3 | <100 | <100 coagulate, wall deposit |
| Dispersion B | 121 | 1 | 500 | 900 coagulate, wall deposit |
| Dispersion B | 100 | 1 | 2000 | 2500 wall deposit |
| Dispersion B | 80 | 5 | 1 · 10$^4$ | 1 · 10$^4$ |

2. Discontinuous (batchwise) sterilization with microwave radiation

Various aqueous multi-phase compositions that contain synthetic resin and have a high initial microbe count are treated batchwise in a microwave unit (MLS 1200, B üchi Laboratoriumstechnik, Göppingen). 10 g of the particular sample are treated in a ®Teflon container for 10 min (Table 2) or for 2 min (Table 3) with microwave beams (2.45 GHz). The temperature that is established is a measure of the intensity of the microwave irradiation.

After the test procedure, the sample containers show neither a wall deposit nor a coagulate, and the colloid-chemical state of the dispersions is not changed by the indirect heating. The samples are transferred to containers under sterile conditions and investigated for microbe contents still present.

TABLE 2

Microbe counts of aqueous multi-phase composition that contain synthetic resin with microwave treatment (10 min, pulsed MW radiation adjusted such that the temperatures stated below area reached)

| Product | Untreated | | Treated with microwaves | | | | | | | |
|---|---|---|---|---|---|---|---|---|---|---|
| | | | 80° C. | | 90° C. | | 100° C. | | 120° C. | |
| | CSA [CFU/ml] | SDA [CFU/ml] | CSA [CFU/ml] | SDA [CFU/ml] | CSA [CFU/ml] | SDA [CFU/ml] | CSA [CFU/ml] | SDA [CFU/ml] | CSA [CFU/ml] | SDA [CFU/ml] |
| Dispersion A | $1 \cdot 10^4$ | $1 \cdot 10^6$ | <100 | <100 | <100 | <100 | <100 | <100 | <100 | <100 |
| Dispersion B | $1 \cdot 10^4$ | $1 \cdot 10^4$ | <100 | <100 | <100 | <100 | <100 | <100 | <100 | <100 |
| Paint $1 \cdot 10^5$ | $1 \cdot 10^5$ | <100 | <100 | <100 | <100 | <100 | <100 | <100 | <100 | <100 |

TABLE 3

Microbe counts of aqueous multi-phase composition that contain synthetic resin with microwave treatment (2 min, pulsed MW radiation adjusted such that the temperatures stated below area reached)

| Product | Untreated | | Treated with microwaves | | | | | | | |
|---|---|---|---|---|---|---|---|---|---|---|
| | | | 60° C. | | 70° C. | | 80° C. | | 90° C. | |
| | CSA [CFU/ml] | SDA [CFU/ml] | CSA [CFU/ml] | SDA [CFU/ml] | CSA [CFU/ml] | SDA [CFU/ml] | CSA [CFU/ml] | SDA [CFU/ml] | CSA [CFU/ml] | SDA [CFU/ml] |
| Dispersion A | $1 \cdot 10^5$ | $1 \cdot 10^4$ | 200 | <100 | 600 | <100 | 400 | <100 | 300 | <100 |
| Dispersion B | $1 \cdot 10^5$ | $1 \cdot 10^5$ | 300 | <100 | 600 | <100 | 500 | 300 | <100 | <100 |

2. Continuous sterilization

The aqueous multi-phase compositions that contain synthetic resin are conveyed from a storage vessel with a self-priming Mohno pump with a low exposure to shear stresses against an increased pressure of 1 bar through the microwave test unit (unit as described above, with two product throughput possibilities on the right and left). The residence time in the microwave heating zone is 10 to 180 sec. The heating zone is followed by a heat-holding zone with residence times of different lengths. The sterilizations are carried out at residence times of 1, 3 and 5 min in the temperature range between 60 and 80° C. The sample temperature is measured directly after the heating zone and at the end of the heat-holding zone. The temperature is regulated by the microwave input and is thus proportional to the intensity of the microwave irradiation.

The results of the experiments with various products are summarized in Table 4. The microbe count determination is carried out as described above.

TABLE 4

Microbe counts of aqueous multi-phase compositions that contain synthetic resin in a continuous microwave experiment with/without a heat-holding zone (pulsed MW radiation adjusted such that the temperatures stated below are reached, microwave treatment (MW) for 1 minute, throughput 3 l/h, 1.8 bar)

| Temp. [°C.] | MW [min] | MW + heat-holding time [min] | Dispersion A CSA [CFU/ml] | SDA [CFU/ml] | Dispersion B CSA [CFU/ml] | SDA [CFU/ml] |
|---|---|---|---|---|---|---|
| untreated | | | $1 \cdot 10^4$ | $1 \cdot 10^4$ | 3300 | $1 \cdot 10^4$ |
| 60 | 1 | — | 3200 | 1900 | 100 | <100 |
| 60 | 1 | 1 | 3900 | 200 | <100 | <100 |
| 60 | 1 | 3 | 3200 | 200 | <100 | <100 |
| 60 | 1 | 5 | 1300 | 200 | <100 | <100 |
| 70 | 1 | — | <100 | <100 | <100 | <100 |
| 70 | 1 | 1 | <100 | <100 | 300 | <100 |
| 70 | 1 | 3 | <100 | <100 | <100 | <100 |
| 70 | 1 | 5 | 100 | <100 | <100 | <100 |
| 80 | 1 | — | <100 | <100 | <100 | <100 |
| 80 | 1 | 1 | <100 | <100 | <100 | 200 |
| 80 | 1 | 3 | <100 | <100 | 100 | <100 |
| 80 | 1 | 5 | <100 | <100 | 100 | 100 |

The microwave treatment is carried out under an increased pressure of 9 bar in the continuously operated unit described. The results of the experiments are summarized in Table 5.

TABLE 5

Microbe counts of aqueous multi-phase compositions that contain synthetic resin in a continuous microwave experiment with/without a heat-holding zone (pulsed MW radiation adjusted such that the temperatures stated below are reached, microwave treatment (MW) for 1 minute, throughput 3 l/h, 9 bar)

| Temp. [°C.] | MW [min] | MW + heat-holding time [min] | Dispersion A CSA [CFU/ml] | Dispersion A SDA [CFU/ml] | Dispersion B CSA [CFU/ml] | Dispersion B SDA [CFU/ml] |
|---|---|---|---|---|---|---|
| untreated | | | $1 \cdot 10^4$ | $1 \cdot 10^4$ | 3300 | $1 \cdot 10^4$ |
| 70 | 1 | — | <100 | <100 | <100 | <100 |
| 70 | 1 | 1 | <100 | <100 | <100 | <100 |
| 70 | 1 | 3 | <100 | <100 | <100 | <100 |
| 70 | 1 | 5 | <100 | <100 | <100 | <100 |

In another experiment, a paint which has been attacked by microorganisms is treated with dielectric radiation in the continuously operated microwave unit described. The results are summarized in Table 6.

TABLE 6

Microbe counts of an aqueous multi-phase compositions that contain synthetic resin in the form of a paint in a continuous microwave experiment with/without a heat-holding zone (pulsed MW radiation adjusted such that the temperatures stated below are reached, microwave treatment (MW) for 1 minute, throughput 3 l/h, 1.8 bar)

| Temp. [°C.] | MW [min] | MW + heat-holding time [min] | Paint CSA [CFU/ml] | Paint SDA [CFU/ml] |
|---|---|---|---|---|
| untreated | | | $1 \cdot 10^5$ | $1 \cdot 10^4$ |
| 50 | 1 | — | $1 \cdot 10^5$ | $1 \cdot 10^4$ |
| 50 | 1 | 3 | $1 \cdot 10^5$ | $1 \cdot 10^4$ |
| 60 | 1 | — | 900 | 800 |
| 60 | 1 | 3 | 800 | 900 |
| 70 | 1 | — | 200 | <100 |
| 70 | 1 | 3 | 300 | <100 |
| 80 | 1 | — | <100 | <100 |
| 80 | 1 | 3 | <100 | <100 |

The results of the studies show that a reduction in microbe counts from $10^6$ CFU/ml to a few hundred microbes or even to below the detection limit is possible by microwave treatment of various aqueous multi-phase compositions that contain synthetic resin even at temperatures above 60° C. and significantly below 100° C. The results also show that the destruction of the microorganisms primarily depends on the intensity of the microwave radiation. The length of the heat-holding zone evidently plays only a minor role. Sterilization with the aid of microwave radiation and higher pressures also leads to a microbe reduction to below the detection limit without the properties of the product being adversely affected.

No formation of deposit on the internal walls of the pipeline of the pilot plant is detected in the continuously-operated microwave irradiation experiment. The products are damaged in their product-specific properties neither by the continuous microwave irradiation nor by the discontinuous microwave irradiation.

What is claimed is:

1. A process for treating a microbially-contaminated aqueous multi-phase composition that contains synthetic resin, the process including the steps of:
   providing an aqueous multi-phase composition that contains a synthetic resin;
   microwave heating the aqueous multi-phase composition under an autogenous pressure of up to 10 bar to destroy microbes therein; and
   immediately transferring the heated aqueous multi-phase composition into containers under substantially sterile conditions.

2. A process as claimed in claim 1, wherein the dielectric heating is carried out by means of a microwave apparatus.

3. A process as claimed in claim 2, wherein the microwave apparatus is operated at a frequency is 0.04 to 24 GHz to achieve microwave heating.

4. A process as claimed in claim 2, wherein the aqueous multi-phase composition flows continuously through the microwave apparatus.

5. A process as claimed in claim 1, wherein the aqueous multi-phase composition is subjected by the microwave heating to a sterilization temperature of below 121° C.

6. A process as claimed in claim 5, wherein the sterilization temperature is between 50° and 100° C.

7. A process as claimed in claim 1, wherein the aqueous multi-phase composition comprises a polymer dispersion.

8. A process as claimed in claim 7, wherein the polymer dispersion comprises an emulsion polymer that contains acrylate or vinyl acetate groups.

9. A process as claimed in claim 1, wherein the aqueous multi-phase composition is a formulation that contains a polymer dispersion.

10. A process of treating a microbially-contaminated aqueous multi-phase composition that contains synthetic resin, the process including the steps of:
    providing an aqueous multi-phase composition that contains a synthetic resin;
    microwave heating the aqueous multi-phase composition to destroy microbes therein; and
    adding a microbicide to the aqueous multi-phase composition, the amount of microbicide added being less than 50% of the amount of microbicide necessary to achieve sterilization for an identical aqueous multi-phase composition which has not been subjected to microwave heating.

11. A process for treating a microbially-contaminated aqueous multi-phase composition that contains synthetic resin, the process including the steps of:
    providing an aqueous multi-phase composition that contains a synthetic resin selected from the group consisting of homo- and copolymeric polyvinyl acetates, polymers of esters of acrylic acid or methacrylic acid with and without a protective colloid, polystyrene, copolymers of styrene and esters of acrylic/methacrylic acid, polybutadiene and copolymers of styrene and butadiene, and aqueous dispersions of polycondensation products; and
    microwave heating the aqueous multi-phase composition under an autogenous pressure of up to 10 bar to destroy microbes therein.

12. A process as claimed in claim 11, wherein the microwave heating is carried out by means of a microwave apparatus.

13. A process as claimed in claim 12, wherein the microwave apparatus of operated at a frequency is 0.04 to 24 GHz to achieve microwave heating.

14. A process as claimed in claim 12, wherein the aqueous multi-phase composition flows continuously through the microwave apparatus.

15. A process as claimed in claim 11 wherein the aqueous multi-phase composition is subjected by the microwave heating to a sterilization temperature of below 121° C.

16. A process as claimed in claim 15, wherein the sterilization temperature is between 50° and 100° C.

17. A process as claimed in claim 11, wherein the aqueous multi-phase composition comprises a polymer dispersion.

18. A process as claimed in claim 17, wherein the polymer dispersion comprises an emulsion polymer that contains acrylate or vinyl acetate groups.

19. A process as claimed in claim 11, wherein the aqueous multi-phase composition is a formulation that contains a polymer dispersion.

20. A process as claimed in claim 11, wherein the microwave heating is carried out immediately before the aqueous multi-phase composition is transferred to containers under largely sterile conditions.

21. A process as claimed in claim 11, wherein the copolymeric polyvinyl acetate comprises a vinyl acetate/maleic acid ester.

22. A process of sterilizing a microbially-contaminated aqueous multi-phase composition that contains synthetic resin, the process including the steps of:

providing an aqueous multi-phase composition that contains a synthetic resin; and sterilizing the aqueous multi-phase composition by microwave heating under an autogenous pressure of up to 10 bar.

* * * * *